United States Patent
Jackson et al.

(10) Patent No.: US 6,897,329 B2
(45) Date of Patent: May 24, 2005

(54) PROCESS FOR THE PREPARATION OF NICKEL/PHOSPHOROUS LIGAND CATALYST FOR OLEFIN HYDROCYANATION

(75) Inventors: Scott C. Jackson, Wilmington, DE (US); Ronald J. McKinney, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 87 days.

(21) Appl. No.: 10/341,860

(22) Filed: Jan. 14, 2003

(65) Prior Publication Data

US 2004/0138494 A1 Jul. 15, 2004

(51) Int. Cl.$^7$ .......................... C07F 15/04; B01J 31/00; C07C 255/00
(52) U.S. Cl. .......................... 556/18; 558/338; 502/155
(58) Field of Search .......................... 556/18; 558/338; 502/155

(56) References Cited

U.S. PATENT DOCUMENTS

| | | | |
|---|---|---|---|
| 3,846,461 A | 11/1974 | Shook, Jr. ............... | 260/439 R |
| 3,846,474 A | 11/1974 | Mok | |
| 3,903,120 A | 9/1975 | Shook, Jr. et al. ...... | 260/439 R |
| 5,061,669 A | 10/1991 | Puckette | |
| 5,512,695 A | 4/1996 | Kreutzer et al. ............ | 558/338 |
| 5,512,696 A | 4/1996 | Kreutzer et al. ............ | 558/338 |
| 5,523,453 A | 6/1996 | Breikss ........................ | 558/338 |
| 5,532,374 A | 7/1996 | Lee et al. | |
| 5,543,536 A | 8/1996 | Tam ............................ | 556/13 |
| 5,663,369 A | 9/1997 | Kreutzer et al. ............ | 549/212 |
| 5,688,986 A | 11/1997 | Tam et al. .................. | 558/338 |
| 5,693,843 A | 12/1997 | Breikss et al. .............. | 558/338 |
| 5,723,641 A | 3/1998 | Tam et al. .................... | 556/13 |
| 5,847,191 A | 12/1998 | Bunel et al. | |
| 5,856,555 A | 1/1999 | Huser et al. ................. | 558/338 |
| 5,959,135 A | 9/1999 | Garner et al. ............... | 558/338 |
| 6,120,700 A | 9/2000 | Foo et al. .................. | 252/182.3 |
| 6,171,996 B1 | 1/2001 | Garner et al. ............... | 502/162 |
| 6,171,997 B1 | 1/2001 | Foo et al. .................... | 502/162 |
| 6,284,865 B1 | 9/2001 | Tam et al. | |
| 6,399,534 B2 | 6/2002 | Bunel et al. ................. | 502/155 |

FOREIGN PATENT DOCUMENTS

| | | |
|---|---|---|
| WO | WO 9530680 | 11/1995 |
| WO | WO 01/14392 | 3/2001 |
| WO | WO 02053527 | 7/2002 |
| WO | WO 03/045555 | 6/2003 |

*Primary Examiner*—Porfirio Nazario-Gonzalez

(57) ABSTRACT

A process for preparing a hydrocyanation catalyst comprising contacting a bidentate phosphorous-containing ligand with nickel chloride in the presence of a nitrile solvent and a reducing metal which is more electropositive than nickel the nickel chloride being introduced as an aqueous solution and the water being removed concurrently with the reduction reaction by azeotropic distillation.

11 Claims, No Drawings

PROCESS FOR THE PREPARATION OF NICKEL/PHOSPHOROUS LIGAND CATALYST FOR OLEFIN HYDROCYANATION

FIELD OF THE INVENTION

This invention relates to a process for the preparation of a hydrocyanation catalyst which is a complex of nickel and a bidentate phosphorous compound.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phoshite and phosphinite ligands can be used to form nickel-based catalysts to perform such hydrocyanation reactions.

U.S. Pat. No. 3,903,120 discloses a process for preparing zero-valent nickel complexes by reacting elemental nickel with a monodentate phosphorous ligand of the formula $PZ_3$ where Z is an alkyl or alkoxy group, or preferably an aryloxy group. The process uses finely divided elemental nickel and is preferably carried out in the presence of a nitrile solvent. The reaction is carried out in the presence of excess ligand.

U.S. Pat. No. 3,846,461 discloses a process for preparing zero-valent nickel complexes of triorganophosphites by reacting triorganophosphite compounds with nickel chloride in the presence of a finely divided reducing metal which is more electropositive than nickel, and in the presence of a promoter selected from the group consisting of $NH_3$, $NH_4X$, $Zn(NH_3)_2X_2$, and mixtures of $NH_4X$ and $ZnX_2$, where X is a halide. Reducing metals include Na, Li, Mg, Ca, Ba, Sr, Ti, V, Fe, Co, Cu, Zn, Cd, Al, Ga, In, Sn, Pb, and Th, with Zn being preferred.

U.S. Pat. No. 5,523,453 discloses a method of preparing nickel hydrocyanation catalysts containing bidentate phosphorous ligands. Zero-valent nickel compounds that contain ligands that can be displaced by the bidentate phosphorous ligand are a preferred source of nickel. Two such compounds are $Ni(COD)_2$, where COD is 1,5-cyclooctadiene, and $(oTTP)_2Ni(C_2H_4)$, where oTTP is $P(O\text{-}ortho\text{-}C_6H_4CH_3)_3$.

Pending U.S. application having the Ser. No. 09/994,102 describes a process for producing a catalyst by contacting divalent nickel compounds with reducing agents. In the disclosed process, the nickel compounds are dried prior to introduction to the reactor. The application describes that the rate of catalyst production increases with increasing temperature, but the amount of ligand degradation and byproduct formation also increases. Accordingly, there is a need for a process that allows for high reaction rates, low degradation, and byproduct formation and the advantage of less expensive drying equipment.

SUMMARY OF THE INVENTION

A process for preparing a hydrocyanation catalyst comprising contacting at least one bidentate phosphorus-containing ligand selected from the group consisting of bidentate phosphites and bidentate phoshinites, with nickel chloride, in the presence of a nitrile solvent, and a reducing metal that is more electropositive than nickel, wherein the nickel chloride is introduced as an aqueous solution wherein (i) the water is removed concurrently with the reduction of the nickel chloride by azeotropic distillation or (ii) the water is removed by azeotropic distillation, followed by reduction of the $NiCl_2$.

DETAILED DESCRIPTION OF THE INVENTION

The catalysts of the present invention may be prepared by contacting nickel chloride with a bidentate phosphorous-containing ligand in the presence of nitrile solvent and a reducing metal. The nickel chloride is introduced as an aqueous solution and the water is removed concurrently with $NiCl_2$ reduction. The reducing metal can be any metal which is more electropositive than nickel. Such metals include Na, Li, K, Mg, Ca, Ba, Sr, Ti, V, Fe, Co, Cu, Zn, Cd, Al, Ga, In, and Sn. Most preferred are Fe and Zn. The reducing metal (hereinafter "MET") is preferably finely-divided. The expression "finely-divided" means that the metal is of a particle size of less than 20 mesh.

The source of nickel for this invention is nickel (II) chloride or $NiCl_2$ dissolved in water. The aqueous solution is available commercially as an approximately 29 weight percent $NiCl_2$ aqueous solution. However, it is believed that the invention is not limited to this weight percentage and aqueous solutions with different weight percent $NiCl_2$ will work. For practical reasons, the preferred aqueous solution contains 20 to 31 weight percent $NiCl_2$. The lower limit is due to cost effectiveness of dehydrating a dilute solution. The upper limit is due to $NiCl_2$ solubility at ambient temperature, particularly due to the precipitation of $NiCl_2(H_2O)_6$.

In contrast to anhydrous $NiCl_2$, since the $NiCl_2$ is already dissolved, the reaction rate is very fast. Unfortunately, the ligand is susceptible to hydrolysis and therefore the water must be removed to prevent ligand degradation. It has been discovered that this water can be removed from the reaction system concurrently with the $NiCl_2$ reduction reaction by azeotropic distillation with nitrile solvent. This is usually carried out below atmospheric pressure in order to reduce the boiling point of the azeotrope and to limit ligand and catalyst degradation. The preferred pressure ranges are from about 0.01 psia to 3 psia (0.07 to 20 kPa). The most preferred pressure ranges are from 0.01 psia to 1.5 psia (0.07 to 10 kPa). Other methods for drying $NiCl_2$ before the reaction are described in pending U.S. application having the Ser. No. 09/994,102.

The catalyst formation reaction is carried out in the presence of a solvent that is a nitrile, preferably 3-pentenenitrile or 2-methyl-3-butenenitrile. The concentration of ligand may range from about 1% to 90% by weight. For practical reasons the preferred range of ligand concentration is 5% to 50%. The extent of reaction may be controlled by making either the $NiCl_2$ or the reducing metal (MET) the limiting reagent. The preferred amount of MET will generally fall in the range of 0.1% to 5% of the reaction mass. The molar ratio of $NiCl_2$ to MET ranges from 0.1:1 to 100:1. The preferred ratio of $NiCl_2$:MET ranges from 0.5:1 to 2:1. The reaction temperature may range from 0° C. to 80° C. The preferred temperature range is 20° C. to 60° C. The reaction may be run in batch or continuous mode.

Suitable ligands for the present invention are bidentate phosphorous-containing ligands selected from the group consisting of bidentate phosphites, and bidentate phosphinites. Preferred ligands are bidentate phosphite ligands.

The preferred bidentate phosphite ligands are of the following structural formulae:

II

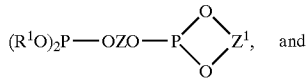

III

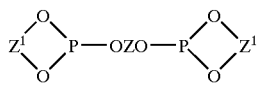

wherein $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

IV

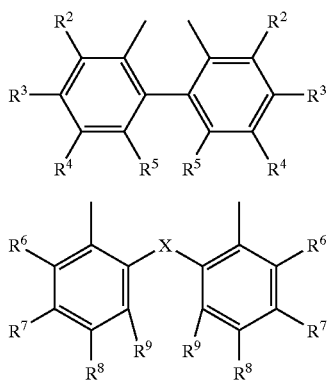

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

VI

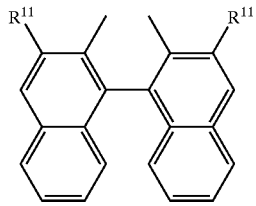

VII

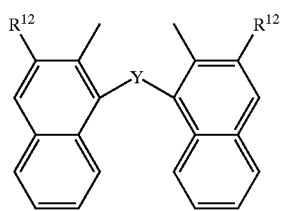

and wherein
$R^{11}$ and $R^{12}$ are independently selected from the group consisting of H, $C_1$ to $C_{12}$ alkyl, and $C_1$ to $C_{12}$ alkoxy; and $CO_2R^{13}$,
$R^{13}$ is $C_1$ to $C_{12}$ alkyl or $C_6$ to $C_{10}$ aryl, unsubstituted or substituted, with $C_1$ to $C_4$ alkyl;
Y is O, S, or $CH(R^{14})$;
$R^{14}$ is H or $C_1$ to $C_{12}$ alkyl;

VIII

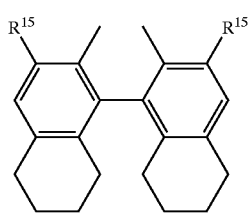

wherein $R^{15}$ is selected from the group consisting of H, $C_1$ to $C_{12}$ alkyl, and $C_1$ to $C_{12}$ alkoxy and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl, and $C_1$ to $C_{12}$ alkoxy groups may be straight chain or branched.

Examples of bidentate phosphite ligands that are useful in the present process include those having the formulae IX to XXXII, shown below wherein for each formula, $R^{17}$ is selected from the group consisting of methyl, ethyl or isopropyl, and $R^{18}$ and $R^{19}$ are independently selected from H or methyl:

IX

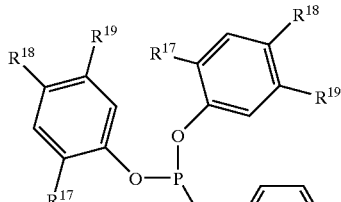

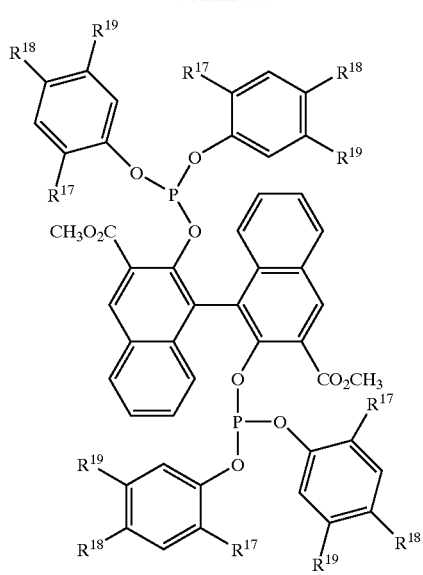
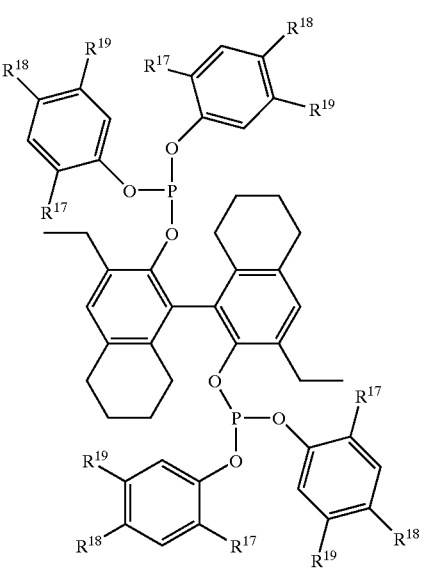
X
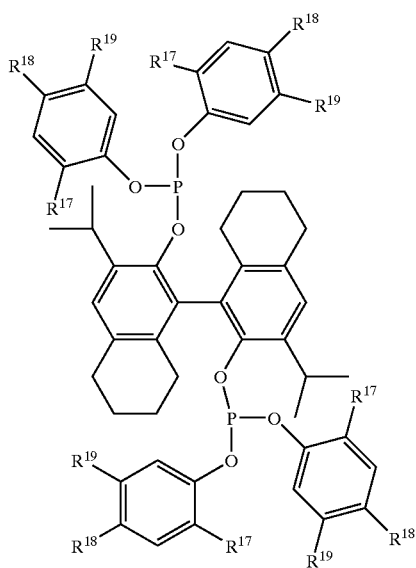
XI
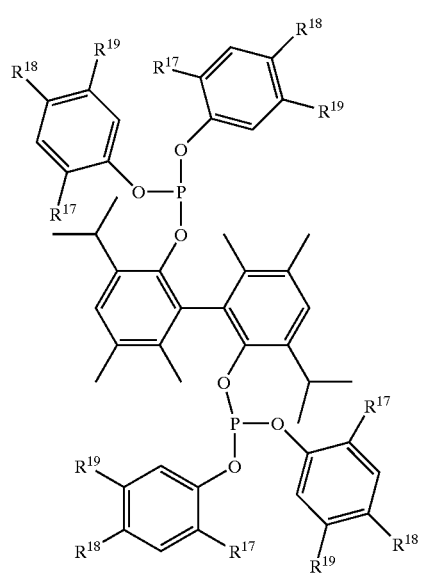
XII
XIII

XIV
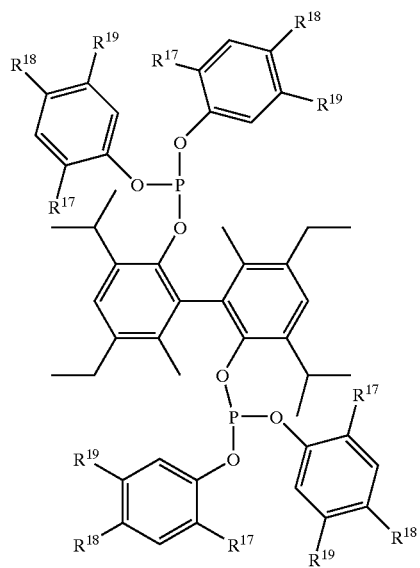
XV
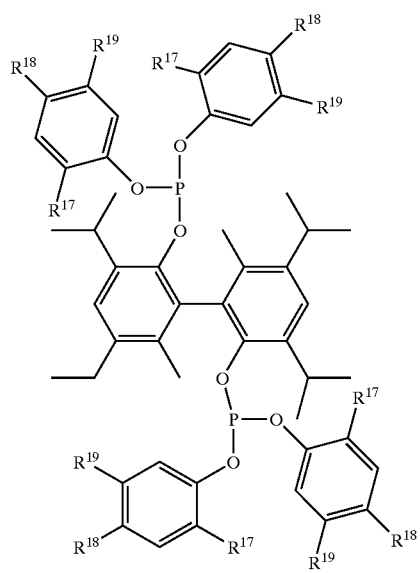
XVI
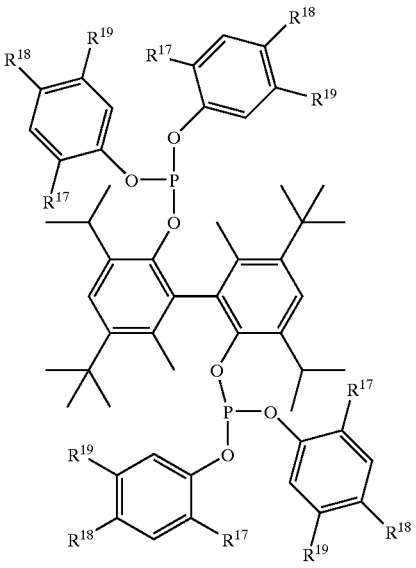
XVII
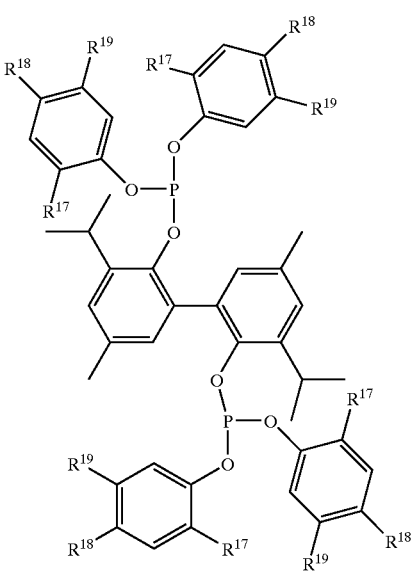

XVIII
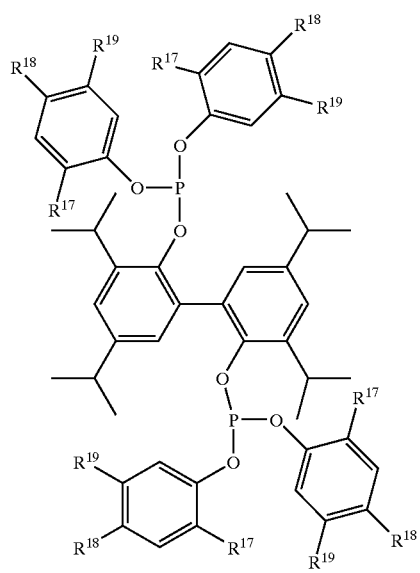
XIX
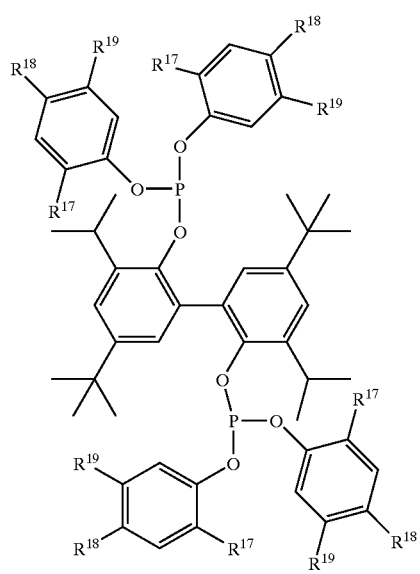
XX
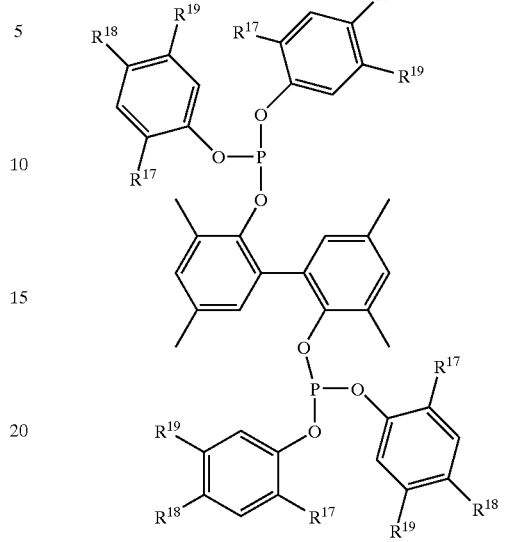
XXI
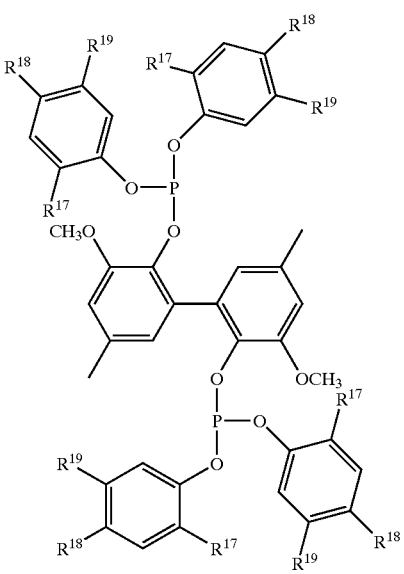

XXII
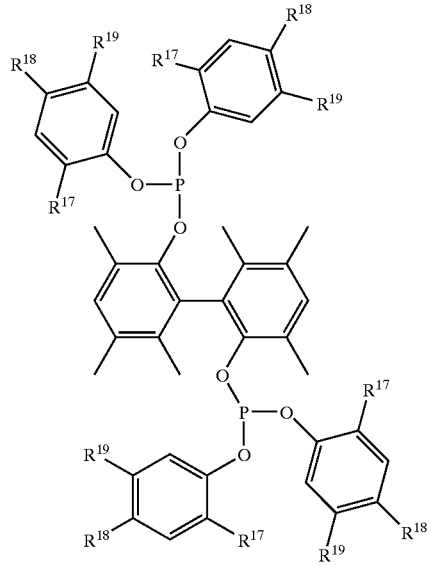
XXIV
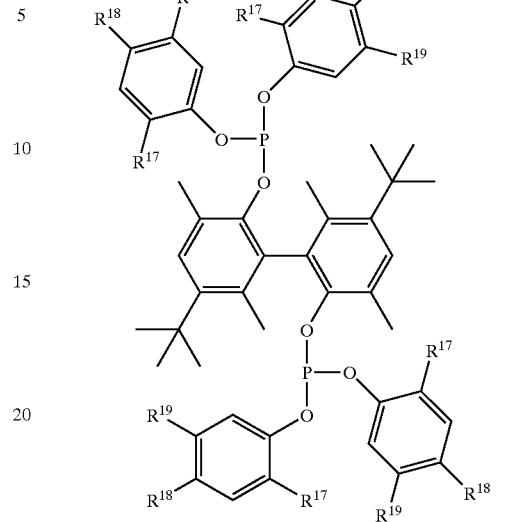
XXIII
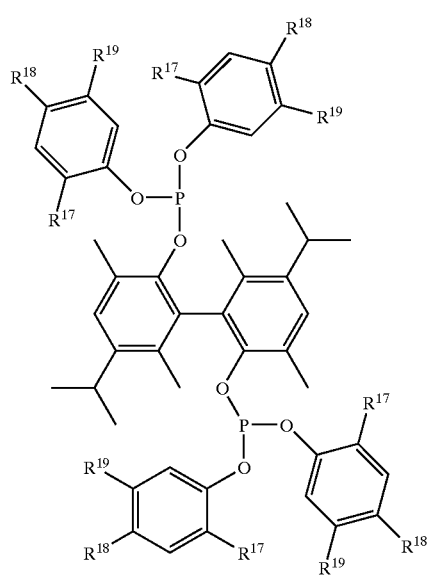
XXV
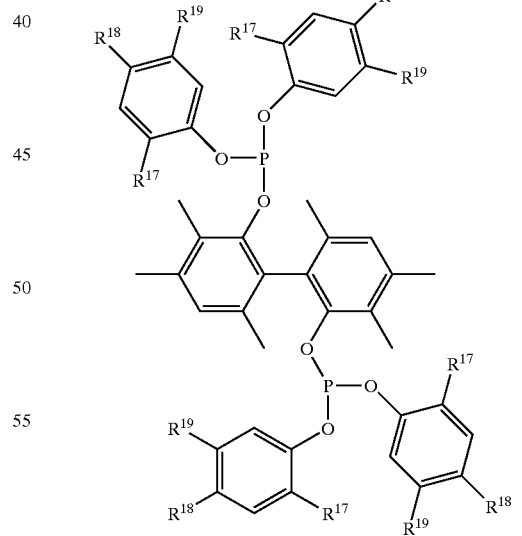

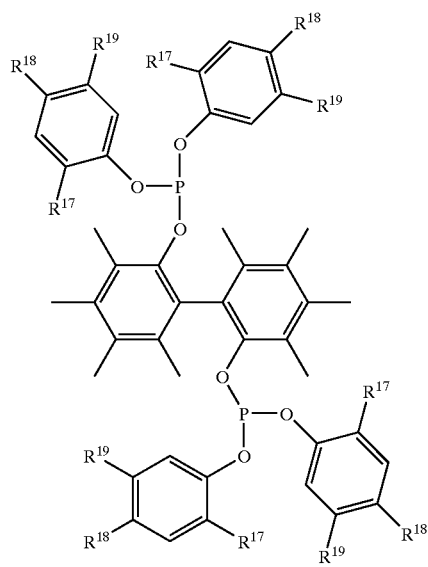
XXVI
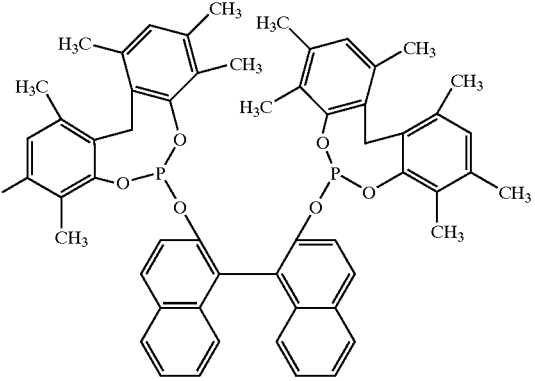
XXIX
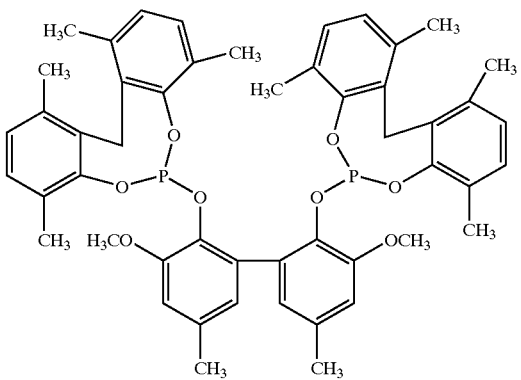
XXX
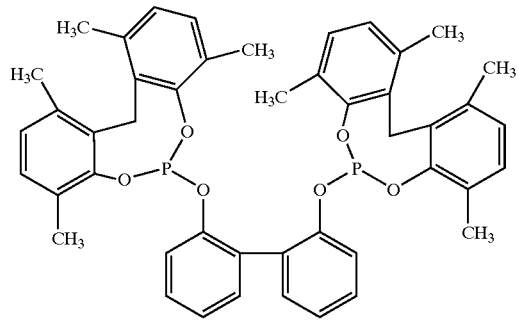
XXVII
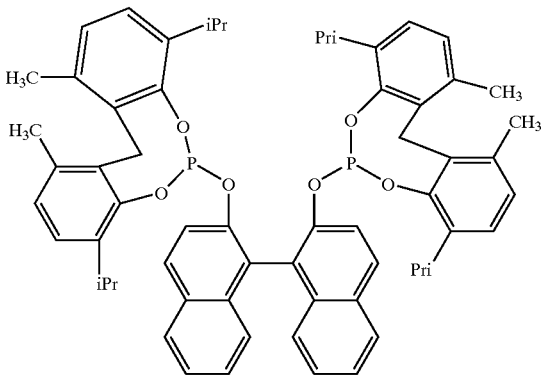
XXXI
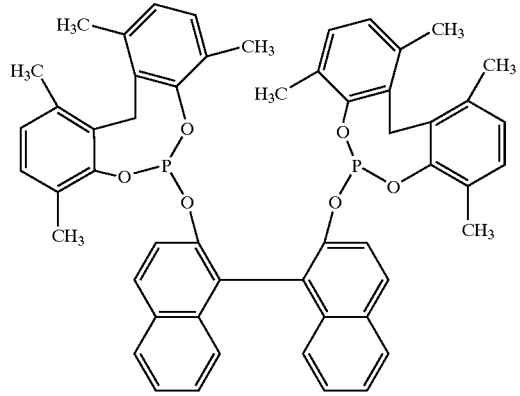
XXVIII
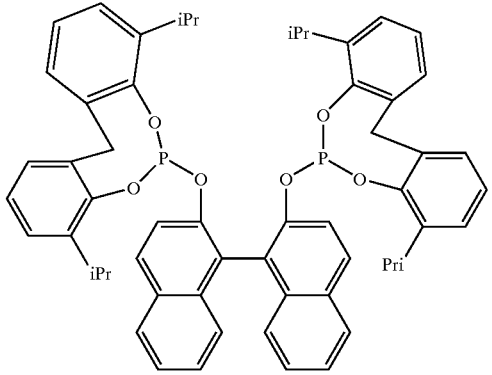
XXXII Additional suitable bidentate phosphites are of the type disclosed in U.S. Pat. Nos. 5,512,695; 5,512,696; 5,663,369; 5,688,986; 5,723,641; 5,847,101; 5,959,135; 6,120,700; 6,171,996; 6,171,997; 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

The reaction may be carried out in a manner such that unreacted excess $NiCl_2$ or MET may be separated from the reaction product by filtration or centrifugation or by settling and decantation. The collected excess nickel chloride or MET can then be recycled back to a catalyst preparation reactor. The catalyst of this invention may be used with 3-pentenenitrile and HCN to produce adiponitrile.

EXAMPLES

The invention is illustrated by the following non-limiting examples.

Example 1 illustrates azeotropoic drying of aqueous $NiCl_2$ followed by reduction using zero valent iron to produce active catalyst. Example 2 illustrates simultaneous drying of aqueous NiCl2 and reduction using zero-valent iron to produce active catalyst.

Example 1

A 250 ml round bottom flask was set up with condenser for liquid take off, a ligand addition funnel, agitator, a septum port, thermocouple, pressure transducer and vacuum throttle valve to control pressure. An electric heating mantel provided heat to the round bottom flask. All fittings were vacuum tight ground glass joints. 120 ml of fresh 3-pentenenitrile was loaded under nitrogen in the addition funnel. 1.4 grams of a 30 wt % aqueous solution NiCl2 was loaded into a gas tight syringe with a valve between the needle and the syringe body. 120 grams of 3-pentenenitrile plus 16.24 grams of ligand with a structure of IX (where $R^{17}$ is isopropyl, $R^{18}$ is H, and $R^{19}$ is methyl), above, was loaded into the round bottom flask. Pumping and purging with nitrogen three times degassed the system. Heat was applied to the flask with agitation. The pressure was adjusted to ~1.7 psia (11.7 kPa). The 3-pentenenitrile started to reflux at ~80.2° C. at this pressure. The needle on the gas tight syringe was stuck into the headspace of the reactor through the septum. The aqueous $NiCl_2$ was drop wise added to the boiling 3-pentenenitrile. Water and 3-pentenenitrile was taken off into an empty graduated cylinder through the condenser. Fresh 3-pentenenitrile was added periodically from the addition funnel to make up for the loss of 3-pentenenitrile that came over with the water. The drop wise addition of the NiCl2 continued until all the NiCl2 had been added to the pot. The pot was allowed to cool to 62° C. under a nitrogen blanket. A slurry of 5.11 grams of iron plus 10.1 grams of 3-pentenenitrile was added to the pot. Pumping and purging with nitrogen three times degassed the system. Vacuum was pulled on the system again and the 3-pentenenitrile was taken off at 65° C. and a pressure of 0.7 psia (4.8 kPa). After 2 hours the solution had turned a dark brown color. After 6 hours the solution was dark brown with a red tint. Agitation was stopped and the remaining solids were allowed to settle. The clear liquid was withdrawn from the pot. A sample from this clear liquid was treated with CO and analyzed by IR. Its adsorbance at 1987 and 2040 $cm^{-1}$ indicated a molar concentration of 0.022 moles/liter of Ni[0]. The LC analysis showed there was no apparent ligand degradation. Treating a sample of the clear solution with additional 3-pentenenitrile and HCN at 50° C. produced adiponitrile at a rate similar to catalyst produced by alternate methods.

Example 2

A 250 ml round bottom flask was set up with condenser for liquid take off, a liquid addition funnel, agitator, a septum port, thermocouple, pressure transducer and vacuum throttle valve to control pressure. An electric heating mantel provided heat to the round bottom flask. All fittings were vacuum tight ground glass joints. 120 ml of fresh 3-pentenenitrile was loaded under nitrogen in the addition funnel. 1.44 grams of a 30 wt % aqueous solution NiCl2 was loaded into a gas tight syringe with a valve between the needle and the syringe body. 120 grams of 3-pentenenitrile plus 16.49 grams of ligand of structure IX (where $R^{17}$ is isopropyl, $R^{18}$ is H, and $R^{19}$ is methyl), above, plus 6.59 grams of iron was loaded into the round bottom flask. Pumping and purging with nitrogen three times degassed the system. Heat was applied to the flask with agitation. The pressure was adjusted to ~0.1 psia (0.7 kPa). The needle on the gas tight syringe was stuck into the headspace of the reactor through the septum. The aqueous NiCl2 was drop wise added to the boiling 3-pentenenitrile. Water and 3-pentenenitrile was taken off into an empty graduated cylinder through the condenser. The temperature varied between 30.4° C. to 41.5° C. at a pressure of ~0.1 psia (0.7 kPa). Fresh 3-pentenenitrile was added periodically from the addition funnel to make up for the loss of 3-pentenenitrile that came over with the water. The drop wise addition of the NiCl2 continued until all the NiCl2 had been added to the pot. After 69 minutes, the NiCl2 addition was completed. The solution appeared to be a dark brown—yellow color. Heating and vacuum to the pot was turned off. The pot was agitated overnight under a nitrogen blanket with no heat. In the morning agitation was stopped and the remaining solids were allowed to settle. The clear liquid was withdrawn from the pot. A sample from this clear liquid was treated with CO and analyzed by IR. Its adsorbance at 1987 and 2040 $cm^{-1}$ indicated a molar concentration of 0.013 moles/liter of Ni[0]. The LC analysis showed there was no apparent liquid degradation. Treating a sample of the clear solution with additional 3-pentenenitrile and HCN at 50° C. produced adiponitrile at a rate similar to catalyst produced by alternate methods.

What is claimed:

1. A process for preparing a hydrocyanation catalyst comprising contacting at least one bidentate phosphorus-containing ligand selected from the group consisting of bidentate phosphites and bidentate phoshinites, with nickel chloride, in the presence of a nitrile solvent, and a reducing metal that is more electropositive than nickel, wherein the nickel chloride is introduced as an aqueous solution wherein (i) the water is removed concurrently with the reduction of the nickel chloride by azeotropic distillation or (ii) the water is removed by azeotropic distillation, followed by reduction of the $NiCl_2$.

2. The process of claim 1 wherein the bidentate phosphorus-containing ligand is a bidentate phosphite.

3. The process of claim 2 wherein the reducing metal is selected from the group consisting of Na, Li, K, Mg, Ca, Ba, Sr, Ti, V, Fe, Co, Cu, Zn, Cd, Al, Ga, In, and Sn.

4. The process of claim 3 further comprising separating unreacted nickel chloride or reducing metal from the hydrocyanation catalyst.

5. The process of claim 3 wherein the reducing metal is Zn or Fe.

6. The process of claim 2 wherein the catalyst preparation is conducted at a temperature of 0° C. to 80° C. and at a pressure of about 0.07 kPa to about 20 kPa.

7. The process of claim 6 wherein the catalyst preparation is conducted at a temperature of about 20° C. to about 60° C.

8. The process of claim 2 wherein the molar ratio of $NiCl_2$ to the reducing metal is 0.1:1 to 100:1.

9. The process of claim 8 wherein the molar ratio of $NiCl_2$ to the reducing metal is 0.5:1 to 2:1.

10. The process of claim 9 wherein the bidentate phosphorous-containing ligand is a compound having the formula

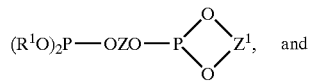

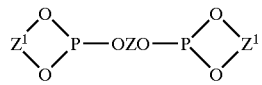

wherein $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

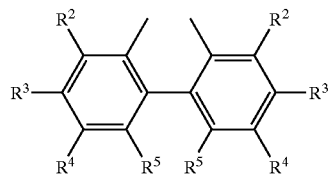

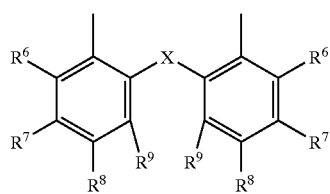

and wherein $R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;

X is O, S, or $CH(R^{10})$;

$R^{10}$ is H or $C_1$ to $C_{12}$ alkyl;

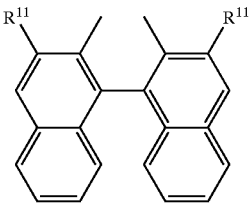

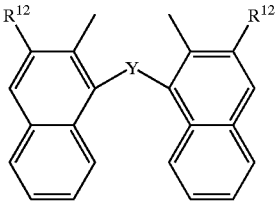

and wherein $R^{11}$ and $R^{12}$ are independently selected from the group consisting of H, $C_1$ to $C_{12}$ alkyl, and $C_1$ to $C_{12}$ alkoxy; and $CO_2R^{13}$, $R^{13}$ is $C_1$ to $C_{12}$ alkyl or $C_6$ to $C_{10}$ aryl, unsubstituted or substituted, with $C_1$ to $C_4$ alkyl;

Y is O, S, or $CH(R^{14})$;

$R^{14}$ is H or $C_1$ to $C_{12}$ alkyl;

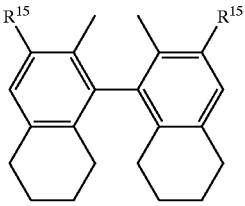

wherein $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl, wherein the structural formulae I through VIII, the $C_1$ to $C_{12}$ alkyl, and $C_1$ to $C_{12}$ alkoxy groups are straight chain or branched.

11. The process of claim 2 wherein said process further comprises contacting the catalyst with 3-pentenenitrile and hydrogen cyanide to produce adiponitrile.

* * * * *